United States Patent [19]

Bolmer

[11] Patent Number: 5,095,158
[45] Date of Patent: Mar. 10, 1992

[54] SOLVENT EXTRACTION OF VDC FROM I-141B

[75] Inventor: Michael S. Bolmer, Lower Providence, Pa.

[73] Assignee: Atochem North America, Inc., Philadelphia, Pa.

[21] Appl. No.: 698,415

[22] Filed: May 10, 1991

[51] Int. Cl.⁵ ............................................. C07C 17/38
[52] U.S. Cl. .................................................. 570/180
[58] Field of Search ........................................ 570/180

[56] References Cited

U.S. PATENT DOCUMENTS 3,947,558  3/1976  Eijl ........................................ 570/180

FOREIGN PATENT DOCUMENTS 492655  5/1953  Canada ................................... 570/180
40-22574 10/1965  Japan .................................... 570/180

*Primary Examiner*—Alan Siegel

[57] ABSTRACT

Partial or total separation of a mixture of vinylidene chloride and 1,1-dichloro-1-fluoroethane by liquid-liquid extraction with solvents having a Hansen solubility parameter of about 30.8–32.0, such as ethanolamine.

2 Claims, 2 Drawing Sheets

I-141b/VDC SEPARATION PROCESS

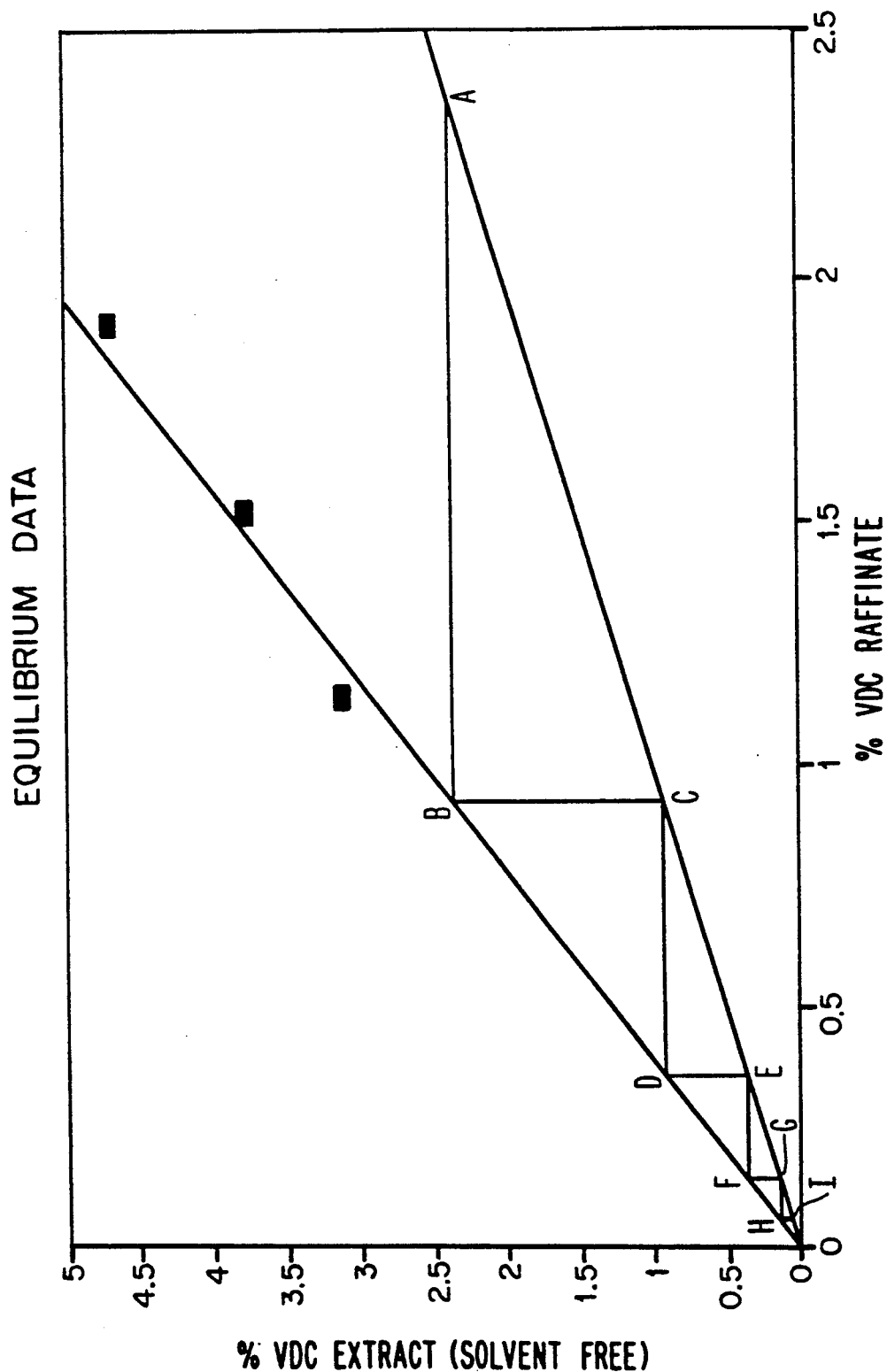

SOLVENT EXTRACTION OF VDC FROM I-141B

FIELD OF THE INVENTION

This invention relates to a method of partially or totally separating a mixture of vinylidene chloride ("VDC") and 1,1-dichloro-1-fluoroethane ("I-141b") by liquid-liquid extraction with solvents having a Hansen solubility parameter of about 30.8–32.0.

BACKGROUND OF THE INVENTION

VDC is an impurity formed during the manufacture of I-141b, a replacement for trichlorofluoromethane as a blowing agent. Since VDC is a suspected carcinogen, a method for its removal is needed, desirably to levels below 500 ppm. Separation by conventional distillation means is extremely difficult, however, since VDC boils at 31° C. and I-141b boils at 32° C.

Removal of VDC by reacting it with chlorine under ultraviolet radiation is disclosed in U.S. Pat. No. 4,948,479, but this requires the consumption of an extra raw material (chlorine) and loss of product to reaction.

While liquid-liquid extraction has been reported in U.S. Pat. No. 4,031,148 for separating chlorinated hydrocarbons by the use of water-miscible solvents and 0–50% water, applicant is not aware of literature which discloses liquid-liquid extraction for separating VDC from HCFC's (hydrochlorofluorocarbons) such as I-141b.

SUMMARY OF THE INVENTION

A method is provided for at least partial separation of a mixture of VDC and I-141b comprising liquid-liquid extraction on the mixture in the presence of an extraction agent (solvent) having a Hansen solubility parameter of from about 30.8 to about 32.0, preferably ethanolamine. More specifically, the process comprises contacting the mixture of I-141b and VDC with the extracting agent such that the agent extracts VDC from the mixture and forms a separate phase therefrom, then separating the phases of VDC-rich solvent and I-141b/VDC mixture, which mixture now has a correspondingly reduced concentration of VDC.

BRIEF DESCRIPTION OF THE DRAWINGS

FIG. 2 shows equilibrium data at 10° C. for the ternary system of VDC, I-141b, and ethanolamine and the use of such data for determining equilibrium stages.

DETAILED DESCRIPTION OF THE INVENTION

Figure 1:
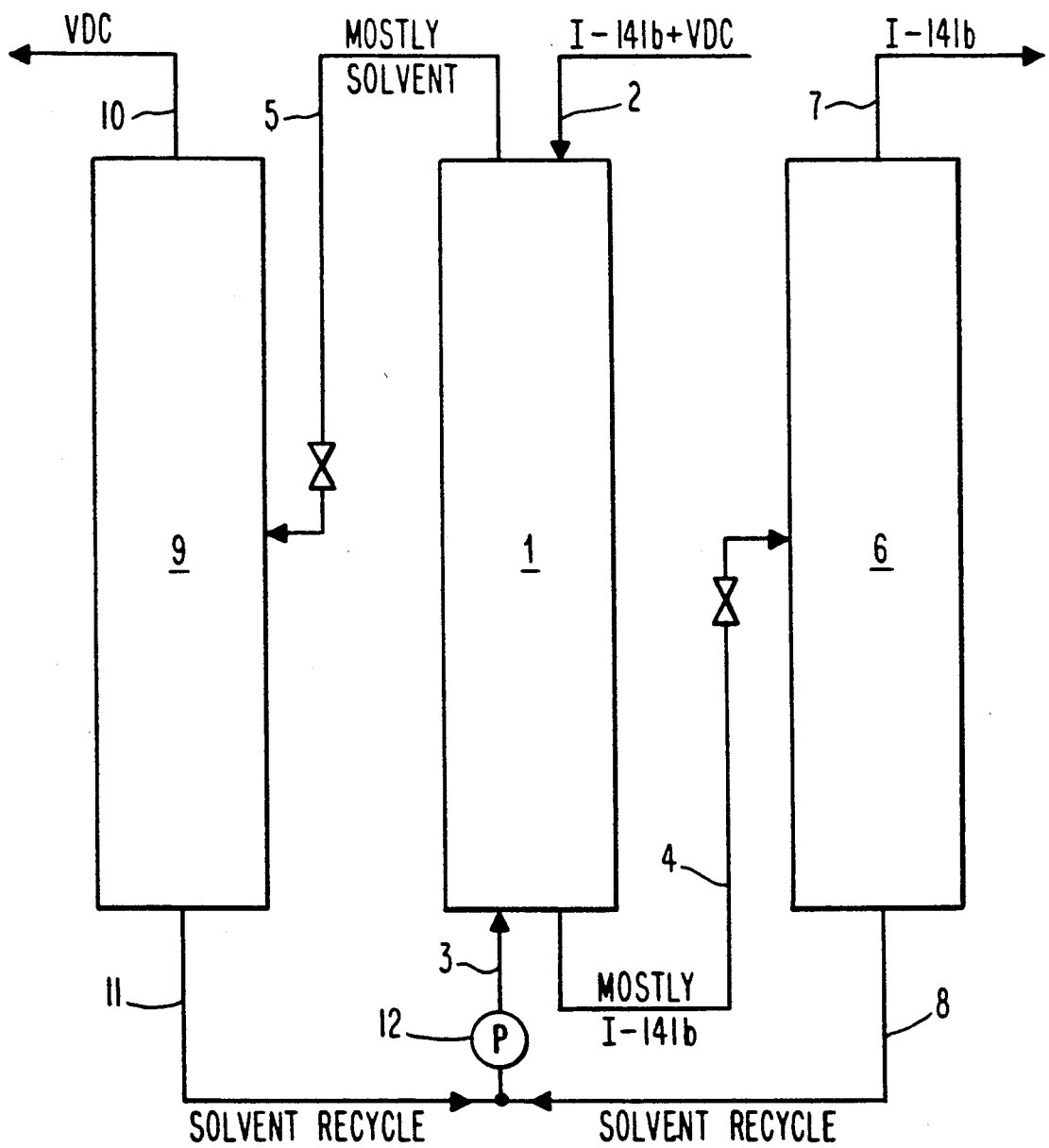
FIG. 1 is a schematic illustration of a liquid-liquid extraction system.

In the manufacture of I-141b by the reaction of hydrogen fluoride and 1,1,1-trichloromethane, the latter is susceptible to dehydrohalogenation, which leads to the formation of VDC as a by-product. I-141b can also be manufactured by the reaction of HF and VDC. In this case conversion of less than 100% leaves unreacted VDC in the product. Since VDC and I-141b have boiling pints within 1° C. of each other, they cannot readily be separated by distillation.

It has now been discovered, however, that efficient separation of VDC and I-141b can be achieved via liquid-liquid extraction using solvents which have a Hansen solubility parameter ("HSP") of from about 30.8 to about 32.0 (a source of such parameters is A. F. Barton, "Handbook of Solubility Parameters and Other Cohesion Parameters", CRC Press, Inc., 1983). Such solvents are generally found to have a selectivity for VDC (at 25° C.) of from about 1.24 to 1.44, while solvents having parameters above or below the 30.8–32.0 range are generally found to have a lower selectivity. For example, while ethanolamine (a preferred solvent of this invention) has an HSP of 31.5 and a selectivity for VDC of 1.44, propylene glycol (HSP of 30.2) and ethylene glycol (HSP of 32.9) have selectivities for VDC of only 1.22 and 1.19, respectively. Solvents of this invention, all of which have selectivities for VDC (at 25° C.) of 1.24–1.44, include ethanolamine; 2-butene-1,4-diol; and mixed solvents consisting of 2-butene-1,4-diol/ethanolamine/dipropylene glycol; ethanolamine/dipropylene glycol; 2-butene-1,4-diol/ethanolamine; ethylene glycol/2-butene-1,4-diol/propylene glycol; ethylene glycol/ethanolamine; ethanolamine/methanol; 2-butene-1,4-diol/methanol; ethylene glycol/dipropylene glycol; and ethylene glycol/ethanol.

The separation can be carried out in a liquid-liquid extractor, as shown in FIG. 1, where a I-141b/VDC mixture is shown as the heavier component entering the top of the extraction column 1 through line 2. The solvent, the lighter component, enters column 1 at the bottom through line 3. The purified (or partially purified) I-141b stream is removed from the bottom of column 1 through line 4, and the used, VDC-enriched, solvent stream is removed from the top of column 1 through line 5. Any solvent adsorbed into the 141b stream is removed by distillation in column 6, producing a purified I-141b stream which exits the top of column 6 through line 7 and a small solvent recycle stream which exits the bottom of column 6 through line 8 for reintroduction to column 1. The used solvent stream is distilled in distillation column 9 to remove the VDC (and any I-141b) which exits at the top of column 9 through line 10, and then the purified solvent stream is recycled back to column 1 via line 11. A pump 12 provides the power to circulate the solvent around the process.

The extraction column can be designed from equilibrium data. For example the Table below shows equilibrium concentrations for the ternary system of VDC, I-141b, and ethanolamine at 10° C. Plotting of the data as in FIG. 2 enables the design of an extraction column to reduce VDC in a I-141b stream from, for example 2.4%, to 0.05%. Referring to FIG. 2, the I-141b is fed to an extraction column (at point A). The solvent leaves the column (at point B) with 2.4% VDC. in equilibrium with I-141b now having a VDC concentration of only 0.9% (point C). Thus, after leaving the first equilibrium stage of the extraction column (from point A to point C), the VDC concentration has been reduced form 2.4% to 0.9%. Using the same procedure (C to E, E to G, and G to I), it is seen that the concentration can be reduced to 0.05% in just four equilibrium stages.

TABLE

| Equilibrium Data for I-141b, VDC, and Ethanolamine at 10° C. (in Mole %) | | | | | |
|---|---|---|---|---|---|
| RAFFINATE | | | EXTRACT | | |
| I-141b | VDC | ETHANOL-AMINE | I-141b | VDC | ETHANOL-AMINE |
| 98.9 | 1.1 | 0.0 | 3.2 | 0.1 | 96.7 |
| 98.5 | 1.5 | 0.0 | 3.6 | 0.1 | 96.2 |
| 98.1 | 1.9 | 0.0 | 5.1 | 0.2 | 94.6 |
| 93.2 | 6.8 | 0.0 | 4.3 | 0.4 | 95.3 |
| 92.4 | 7.6 | 0.0 | 5.3 | 0.5 | 94.2 |
| 88.9 | 11.1 | 0.0 | 5.2 | 1.0 | 93.8 |

TABLE-continued

Equilibrium Data for I-141b, VDC, and Ethanolamine at 10° C. (in Mole %)

| RAFFINATE | | | EXTRACT | | |
|---|---|---|---|---|---|
| I-141b | VDC | ETHANOL-AMINE | I-141b | VDC | ETHANOL-AMINE |
| 88.7 | 11.3 | 0.0 | 4.6 | 1.1 | 94.3 |
| 77.4 | 22.6 | 0.0 | 4.1 | 1.7 | 94.2 |
| 76.8 | 23.2 | 0.0 | 2.8 | 1.3 | 96.0 |
| X* | | | Y* | | |
| 1.1 | | | 3.1 | | |
| 1.5 | | | 3.8 | | |
| 1.9 | | | 4.7 | | |
| 6.8 | | | 8.4 | | |
| 7.6 | | | 8.6 | | |
| 11.1 | | | 16.7 | | |
| 11.3 | | | 19.3 | | |
| 22.6 | | | 29.9 | | |
| 23.2 | | | 31.3 | | |

*-VDC on a solvent-free basis

What is claimed is:

1. A method of at least partial separation of a mixture of vinylidene chloride and 1,1-dichloro-1-fluoroethane comprising liquid-liquid extraction on said mixture in the presence of an extraction agent wherein the extraction agent is selected from the group consisting of ethanolamine; 2-butene-1,4-diol; and mixed solvents consisting of 2-butene-1,4-diol/ethanolamine/dipropylene glycol; ethanolamine/dipropylene glycol; 2-butene-1,4-diol/ethanolamine; ethylene glycol/2-butene-1,4-diol/propylene glycol; ethylene glycol/ethanolamine; ethanolamine/methanol; 2-butene-1,4-diol/methanol; ethylene glycol/dipropylene glycol; and ethylene glycol/ethanol.

2. The method of claim 1 wherein the extraction agent is ethanolamine.

* * * * *